(12) United States Patent
Freeman et al.

(10) Patent No.: US 9,186,408 B2
(45) Date of Patent: Nov. 17, 2015

(54) NITRATED-FATTY ACIDS MODULATION OF TYPE II DIABETES

(71) Applicant: University of Pittsburgh—Of the Commonwealth System of Higher Education, Pittsburgh, PA (US)

(72) Inventors: Bruce A. Freeman, Pittsburgh, PA (US); Francisco J. Schopfer, Pittsburgh, PA (US)

(73) Assignee: University of Pittsburgh—of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 14/244,741

(22) Filed: Apr. 3, 2014

(65) Prior Publication Data
US 2014/0309303 A1 Oct. 16, 2014

Related U.S. Application Data

(63) Continuation of application No. 13/666,827, filed on Nov. 1, 2012, now Pat. No. 8,735,449, which is a continuation of application No. 12/670,951, filed as application No. PCT/US2008/009274 on Aug. 1, 2008, now Pat. No. 8,324,277.

(60) Provisional application No. 60/953,360, filed on Aug. 1, 2007.

(51) Int. Cl.
*A61K 31/201* (2006.01)
*A61K 45/06* (2006.01)
*A61K 31/20* (2006.01)

(52) U.S. Cl.
CPC ............... *A61K 45/06* (2013.01); *A61K 31/20* (2013.01); *A61K 31/201* (2013.01)

(58) Field of Classification Search
CPC .................................................... A61K 31/201
USPC ........................................................ 514/560
See application file for complete search history.

(56) References Cited

U.S. PATENT DOCUMENTS

| 6,187,747 B1 | 2/2001 | Singh et al. |
| 8,324,277 B2 | 12/2012 | Freeman |
| 2006/0100278 A1 | 5/2006 | Cooper et al. |

FOREIGN PATENT DOCUMENTS

| WO | WO 2005/110396 A2 | 11/2005 |
| WO | WO 2006/086727 A2 | 8/2006 |

OTHER PUBLICATIONS

Baker et al., "Fatty Acid Transduction of Nitric Oxide Signaling," *The Journal of Biological Chemistry*, 280(51):42464-42475, Dec. 23, 2005.
Kim et al., "The effect of PPAR-γ agonist on glucose metabolism and insulin sensitivity in on-obese type 2 diabetic rat models," *Diabetes, American Diabetes Association* 55: Suppl. 1, Jun. 1, 2006.
Marx et al., "Peroxisome Proliferator-Activated Receptors and Atherogenesis: Regulators of Gene Expression in Vascular Cells," *Circulation Research*, 94(9):1168-1178, May 14, 2004.
Mitschke et al., "9- and 10-Nitro-oleic acid do not interfere with the GC-MS quantitative determination of nitrate and nitrate in biological fluids when measured as their pentafluorobenzyl derivatives," *Journal of Chromatography*, 85(1):287-291, May 2007. *Abstract.
Ryan et al., "Diabetes and the Mediterranean diet: a beneficial effect of oleic acid on insulin sensitivity, adipocyte glucose transport and endothelium-dependent vasoreactivity," *Q J Med*, 93:85-91, 2000. *Abstract.
Communication pursuant to Article 94(3) EPC for European Application No. 08 780348.2-2123 dated Jul. 26, 2011.
International Search Report for International Application No. PCT/US08/09274 dated Oct. 24, 2008.
Supplementary European Search Report from European Application No. EP 08 78 0348 dated Jul. 30, 2010.
Summons to Attend Oral Proceedings dated Oct. 2, 2012, from corresponding European Patent Application No. 08780348.

*Primary Examiner* — Raymond Henley, III
(74) *Attorney, Agent, or Firm* — Klarquist Sparkman, LLP

(57) ABSTRACT

Nitro oleic acid and related metabolites are agonists of PPAR-γ. Surprisingly, nitro oleic acid is a more potent agonist of PPAR-γ, relative to nitro linoleic acid. Thus, nitro oleic acid and its metabolites, as well as their pharmaceutically acceptable salts and prodrug forms, are candidate therapeutics for the treatment of type-2 diabetes, which results from insulin resistance accompanying the improper functioning of PPAR-γ.

15 Claims, 6 Drawing Sheets

NITRATED-FATTY ACIDS MODULATION OF TYPE II DIABETES

CROSS-REFERENCE TO RELATED PATENT APPLICATIONS

This is a Continuation of U.S. patent application Ser. No. 13/666,827, filed Nov. 1, 2012, now U.S. Pat. No. 8,735,499, which is a continuation of U.S. patent application Ser. No. 12/670,951, filed May 10, 2010, now U.S. Pat. No. 8,324,277, which is the U.S. National Stage of International Application No. PCT/US08/09274, filed Aug. 1, 2008, which was published in English under PCT Article 21(2), which in turn claims the benefit of U.S. Provisional Application No. 60/953,360, filed Aug. 1, 2007, all of which are hereby incorporated by reference.

STATEMENT REGARDING FEDERALLY SPONSORED RESEARCH

This invention was made with United States government support under grant number R01 HL58115, awarded by the National Institutes of Health. The United States government has certain rights in the invention.

BACKGROUND OF THE INVENTION

The present invention relates to the use of nitrated fatty acids as therapeutics for treating type-2 diabetes. Fatty acids are both physiological energy sources and mediators of signaling events involved, for example, in inflammation and in energy homeostasis.

Saturated, unsaturated, and polyunsaturated fatty acids have been identified to date. Unsaturated electrophilic fatty acids have emerged as an important class of endogenous signaling molecules. Within this class are fatty acid hydroperoxides, keto fatty acids, and nitrated fatty acids, among others. For example, see Freeman et al., *Chem. Res. Toxicol.* 12:83-92 (1999), and Lima et al., *Biochemistry* 41:10717-22 (2002).

The signaling ability of nitro fatty acids stems predominantly from their ability to form reversible covalent adducts with nucleophilic centers of cellular proteins that are implicated in various transcriptional and cellular signaling processes. In particular, regulation of signaling activity most often occurs via the covalent modification of an active site thiol group of a protein target.

Recent studies suggest that nitro fatty acids such as 9- or 10-nitro octadecenoic acid ("nitro oleic acid") and the various regioisomers (9-, 10-, 12- and 13-nitro) of nitro linoleic acid are adaptive mediators that play a crucial role in linking disease processes with underlying cellular events. See Freeman et al., *Proc. Nat'l Acad. Sci. USA* 99: 15941-46 (2002). In particular, nitro fatty acids modulate the activity of the peroxisome proliferator activating receptor gamma (PPAR-γ), for example, in response to inflammation and metabolic imbalance.

While both nitro oleic acid and nitro linoleic acid interact with PPAR-γ, little is known about the structural and biochemical determinants that account for their PPAR-γ activity and the related downstream activation of gene transcription. Consequently, no systematic approach exits for the design of pharmacophores that can modulate PPAR-γ activity.

SUMMARY OF THE INVENTION

Accordingly, the present invention provides, in one of its aspects, a pharmaceutical composition comprising (A) an active agent selected from nitro oleic acid and a metabolite of nitro oleic acid, or a pharmaceutically acceptable salt or prodrug of such active agent, and (B) a pharmaceutically acceptable carrier. In a preferred embodiment, the active agent is nitro oleic acid.

In accordance with another of its aspects, the invention provides a method for treating type-2 diabetes, comprising (A) administering to a subject in need thereof a pharmaceutical composition as described above and then (B) repeating step (A) at least once. Preferably, the method further comprises, after at least one repetition of step (A); the monitoring of the subject for a change relating to type-2 diabetes.

Pursuant to yet another aspect of the invention, a method is provided for gauging efficacy of a treatment for type-2 diabetes. This method comprises
(A) obtaining a first and a second sample from a subject suffering from type-2 diabetes, which samples are obtained at different times during said treatment;
(B) determining blood glucose levels in the first and second samples; and
(C) comparing the blood glucose level between the samples. In accordance with these steps, a lower blood glucose level in the second sample is an indicator of efficacy of the treatment.

DETAILED DESCRIPTION OF THE INVENTION

Nitro oleic acid and related metabolic products ("metabolites") are agonists of PPAR-γ. The inventor's discovery that nitro oleic acid is surprisingly more potent as an agonist of PPAR-γ, relative to nitro linoleic acid, underscores the prospect, in accordance with the present invention, of using nitro oleic acid and its metabolites, as well as their pharmaceutically acceptable salts and prodrug forms, as active agents in the treatment of type-2 diabetes, which results from insulin resistance accompanying the improper functioning of PPAR-γ.

The structural determinants responsible for the potency of nitro oleic acid and its metabolites at PPAR-γ were illuminated using a computational model for receptor-ligand interaction. Modeling data indicate that both arginine-288 (Arg288) and cysteine-285 (Cys285), present in the ligand binding pocket of PPAR-γ, are important for binding. For example, the receptor-ligand model indicates an electrostatic interaction between arginine-288 and the anionic nitro group of nitro oleic acid, while Cys285 is found to be in a suitable position for interacting with the olefinic double bond. These observations indicate that nitro oleic acid activates PPAR-γ via the covalent modification of its active site thiol, and compounds that preserve such interactions will activate the receptor in a similar manner, thus qualifying as a candidate therapeutic for treating type-2 diabetes.

Figure 1:
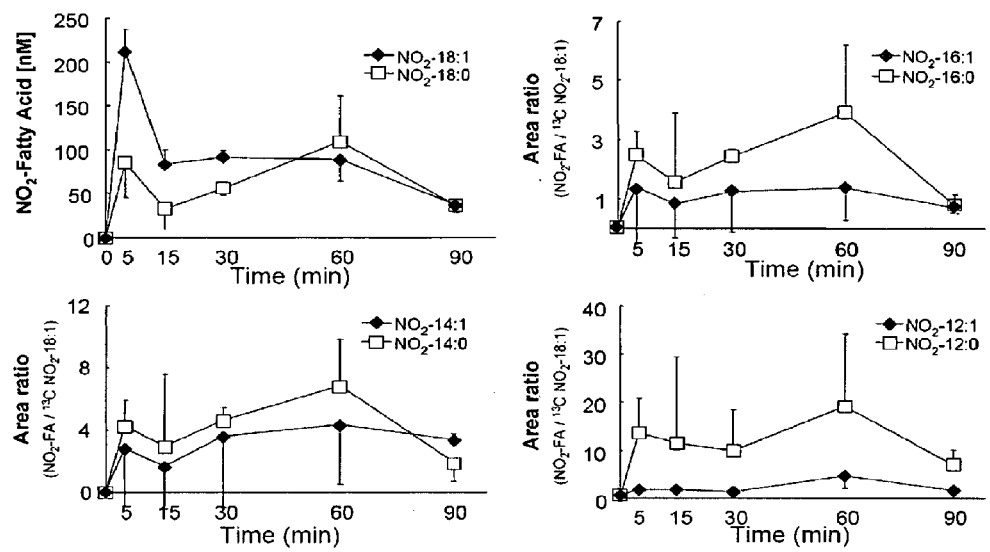
FIG. 1 is a graph depicting serum levels of nitro oleic acid and as its physiological metabolites as a function of time.

Analysis of mouse plasma after intravenous administration of nitro oleic acid illuminates the physiological fate of nitro oleic acid. Nitro oleic acid is converted in-vivo, to its saturated analog, or can undergo β-oxidative cleavage to give several short chain products, such as the corresponding saturated or unsaturated C-10 to C-16 nitrated analogs. FIG. 1 shows the plasma levels of nitro oleic acid or its metabolic products as a function of time. For nitro oleic acid as well as its saturated 18:0 nitrated analog, the curve is biphasic, with peak concentrations occurring at around 5 minutes following the administration of nitro oleic acid. In contrast, the plasma levels for the β-oxidation products are highest at around 60 minutes.

The presence of β-oxidation products in blood plasma has important physiological implications. It is believed that the short-chain metabolites are less hydrophobic than the parent acid. Nevertheless, these compounds preserve the molecular determinants that are believed to be important for binding. Additionally, the smaller size the C-10 to C-16 metabolic products will allow these metabolites to partition differently between the hydrophobic and hydrophilic compartments physiologically. Such differences in partitioning ratios alter the anatomic distribution, chemical reactivity, and pharmacological profiles of these metabolites, by altering their availability to cellular targets. Pursuant to the invention, the C-10 to C-16 metabolites are also suitable candidate therapeutics for the treatment of type-2 diabetes, a condition associated with PPAR-γ dysfunction. See Freeman et al., *Chem. Res. Toxicol.* 12: 83-92 (1999).

Supportive of this anti-diabetic indication, nitro oleic acid was found to improve insulin sensitivity and lower blood glucose levels in ob/ob mice. In particular, in-vivo results indicate that nitro oleic acid reduces blood glucose levels without the side-effects of weight gain and fluid retention associated with Rosiglitazone, a known PPAR-γ agonist.

Figure 2:
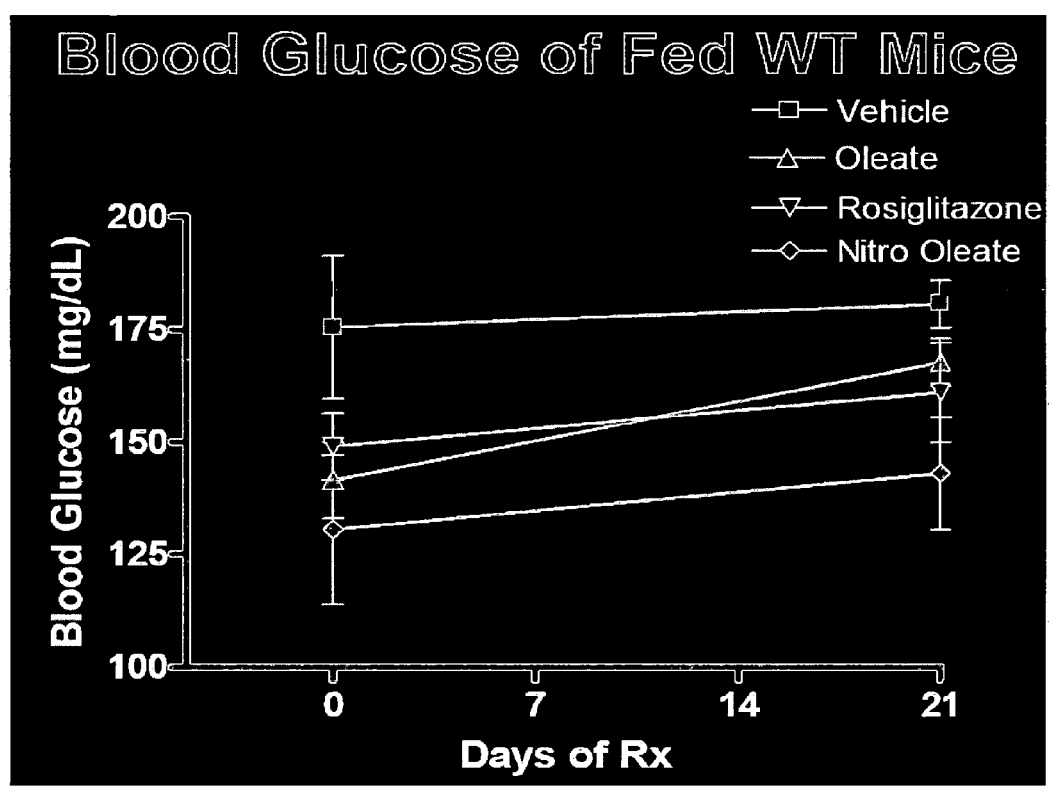
FIG. 2 is a graph that correlates blood glucose levels in wild-type (WT) mice on different days after injection with oleic acid, nitro oleic acid, rosiglitazone, and a vehicle.

As shown in FIG. 2, nitro oleic acid but not oleic acid maintains a steady blood glucose level in fed WT mice. The in-vivo results indicate that nitro oleic acid was at least as effective as Rosiglitazone in maintaining blood glucose levels. Similar results are observed in experiments involving ob/ob mice. As seen from the graph in FIG. 3, both nitro oleic acid and Rosilitazone are effective in reducing blood glucose levels. However, for mice receiving oleic acid the blood glucose levels increased over the course of the study. These results, therefore, provide support for nitro oleic acid's role in lowering blood glucose and as a candidate therapeutic for the treatment of diabetes.

Figure 4:
FIG. 4 is a graph that correlates the body weights of WT and ob/ob mice, undergoing treatment with nitro oleic acid, to the body weight of WT and ob/ob mice that receive oleic acid, rosiglitazone, and a vehicle, respectively.

In addition to reducing blood glucose levels, no increase in body weight is observed when nitro oleic acid is administered to mice. As shown in FIG. 4, the body weights of WT mice receiving nitro oleic acid, or Rosiglitazone do not change over the course of the study (25 days), however, the results are substantially different for ob/ob mice. In this case, the body weight initially decreases for animals receiving nitro oleic acid (days 0-10) and then remains constant over the latter half of the study. In contrast, animals receiving Rosilitazone or oleic acid show a steady increase in body weights over the entire course of the study.

Without endorsement of any particular theory, the absence of weight gain in ob/ob mice is believed to occur because physiologically nitro oleic acid is adduced to plasma, which serves as a "storage system" and temporarily inactivates the nitrated fatty acid, until it is required for facilitating a particular signal transduction event. Since activation of PPAR-γ occurs upon binding free nitro oleic acid, the sequestration of this molecule prevents the aberrant activation of PPAR-γ or the transcription of genes that are regulated by this nuclear receptor.

Figure 5:
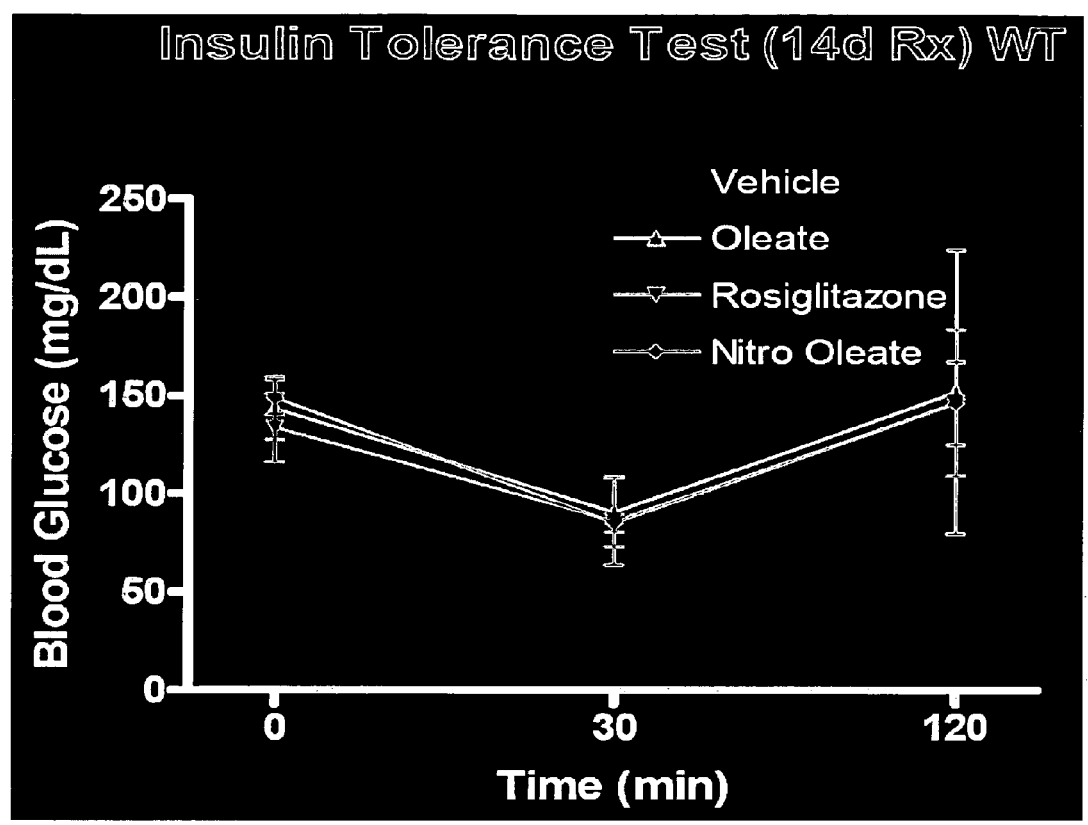
FIG. 5 is a graph that shows the change in insulin sensitivity for WT mice injected with oleic acid, nitro oleic acid, rosiglitazone, and a vehicle, respectively
Figure 6:
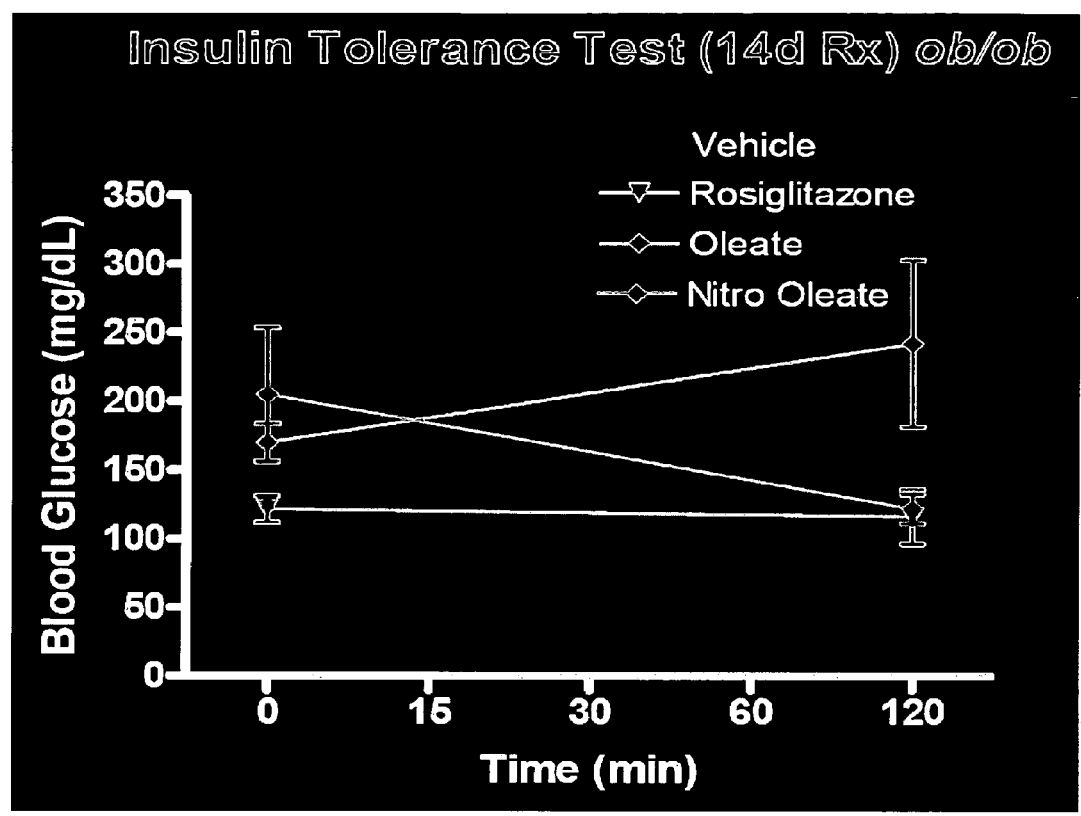
FIG. 6 is a graph that documents a change in insulin sensitivity of ob/ob mice, observed after injection with oleic acid, nitro oleic acid, rosiglitazone, and a vehicle, respectively.

Further evidence, that nitro oleic acid modulates PPAR-γ activity via a binding interaction different from that of Rosiglitazone is provided by the discovery that nitro oleic acid and not Rosiglitazone improves insulin sensitivity in ob/ob mice. In this regard, for WT mice receiving either nitro oleic acid or Rosiglitazone, the administration of insulin results in an initial drop in blood glucose levels followed by an elevation to normal levels shortly after the administration of insulin as shown in FIG. 5. In contrast, as seen by the graph in FIG. 6, administration of nitro oleic acid to ob/ob mice followed by the administration of insulin causes a substantial decrease in blood glucose levels. On the other hand, the blood glucose levels in ob/ob mice receiving Rosiglitazone are unchanged upon administration of insulin. These results indicate that administration of nitro oleic prior to insulin enhances insulin sensitivity in ob/ob diabetic mice, while Rosiglitazone fails to do so. The fact that both nitro oleic acid and Rosiglitazone exert their blood glucose lowering effect through the activation of PPAR-γ, indicates that they interact differently with the receptor and consequently the transcription of genes that regulate metabolic events that lead to weight gain and fluid retention.

The importance of nitro fatty acids as signaling molecules has prompted the development of various procedures for synthesizing these compounds. For example, Brandchaud et al., *Org. Lett.* 8: 3931-34 (2006), and King et al., *Org. Lett.* 8: 2305-08 (2006), disclose syntheses that could be used in the context of the present invention. Another suitable synthesis approach, disclosed in U.S. Patent Publication No. 2007/0232579, involves the direct nitration of an appropriate unsaturated fatty acid. Accordingly, (Z)-octadec-9-enoic acid (oleic acid) is reacted with $NaNO_2$ in the presence of phenylselenium bromide and mercuric chloride under anhydrous conditions to give 9-nitro or 10-nitro oleic acid. A similar synthetic strategy is believed to nitrate the appropriate C-10 to C-16 unsaturated fatty acids to give the corresponding nitro oleic acid metabolic products.

Thus obtained, the synthetic regioisomers of nitro oleic acid or their respective C-10 to C-16 metabolites are typically purified prior to biological use. In one aspect of the invention, therefore, large-scale purification of the individual isomers is carried out using preparative high performance liquid chromatography (HPLC), as described in U.S. Patent Publication No. 2007/0232579. The purified compounds thus obtained are appropriately formulated prior to in vivo administration.

A pharmaceutical composition of the invention can include one or more therapeutic agents in addition to nitro oleic acid or a related compound, as described above. Illustrative of such therapeutics are cytokines, chemokines, and/or regulators of growth factors. Additionally, the invention contemplates a formulation that contains either a single regioisomer or both regioisomers of nitro oleic acid.

The pharmaceutical composition can have more than one physiologically acceptable carrier, too, such as a mixture of two or more carriers. The composition also can include thickeners, diluents, solvents, buffers, preservatives, surface active agents, excipients, and the like.

The pharmaceutical carrier used to formulate the nitro oleic acid of the invention will depend on the route of administration. Administration may be topical (including opthamalic, vaginal, rectal, or intranasal), oral, by inhalation, or parenterally, for example by intravenous drip, subcutaneous, intraperitoneal or intramuscular injection.

Thus, nitro oleic acid or its metabolites can be administered intravenously, intraperitoneally, intramuscularly, subcutaneously, intracavity, transdermally, intratracheally, extracorporeally, or topically (e.g., topical intranasal administration or administration by inhalant). In this regard, the phrase "topical intranasal administration" connotes delivery of the compositions into the nose and nasal passages through one or both of the nares and can comprise delivery by a spraying mechanism or droplet mechanism, or through aerosolization of the nucleic acid or vector. The latter can be effective when a large number of subjects are to be treated simultaneously, where "subject" can denote a human or an non-human animal. Administration of the compositions by inhalant can be through the nose or mouth via delivery by a spray or droplet mechanism. Delivery also can be directed to any area of the respiratory system, such as the lungs, via intubation.

A pharmaceutical composition of the nitro oleic acid and its metabolites for parenteral administration, according to the invention, can include excipients and carriers that stabilize the nitro fatty acid mimetic. Illustrative of such a carrier are non-aqueous solvents, such as propylene glycol, polyethylene glycol, vegetable oils, and injectable organic esters such as ethyl oleate. Additionally, formulations for parenteral administration include liquid solutions, suspensions, or solid forms suitable for solution or suspension in liquid prior to injection, or emulsions.

Intravenous compositions can include agents to maintain the osmomolarity of the formulation. Examples of such agents include sodium chloride solution, Ringer's dextrose, dextrose, lactated Ringer's solution, fluid and nutrient replenishers, and the like. Also included in intravenous formulations are one or more additional ingredients that prevent microbial infection or inflammation, as well as anesthetics.

Alternatively, pharmaceutical compositions of the salt form of nitro oleic acid or its metabolites is administered. Illustrative of such salts are those formed by reaction of the carboxyl group with an inorganic base such as sodium hydroxide, ammonium hydroxide, or potassium hydroxide. Additionally, the salt is formed by reacting the carboxyl group with organic bases such as mono-, di-, trialkyl and aryl amines and substituted ethanolamines.

To address concerns that at physiological pH, nitro oleic acid typically will be a negatively charged molecule, which may have non-optimal bioavailability and cell-transport kinetics, one may provide a compound of the invention formulated as a prodrug. Illustrative of such a prodrug is a pharmaceutically acceptable ester, such as a methyl or an ethyl ester. The ester acts as a prodrug because non-specific intracellular esterase convert it to the active form responsible for eliciting therapeutic effect.

Type-2 diabetes is a chronic condition that results from a loss of sensitivity to insulin. As described above, a pharmaceutical composition of the invention improves insulin sensitivity and, hence, can serve as a therapeutic for treating type-2 diabetes. Successful treatment of type-2 diabetes typically entails as well an ongoing monitoring of the subject for changes related to the diabetic condition, e.g., monitoring physiological levels of different metabolic parameters associated with this condition. Thus, the subject's blood and urine glucose levels can be measured to assess how frequently to administer the inventive composition. Additional markers such as a gain in body weight, frequency of urination and the levels of glucagon in the blood can be used to monitor and possibly to modify treatment to best suit the given subject.

In support of such an anti-diabetic regimen, the present invention also provides for using one of the above-mentioned active agents to prepare a pharmaceutical composition for treating type-2 diabetes in a subject. To this end, different formulation approaches have been described above.

Figure 3:
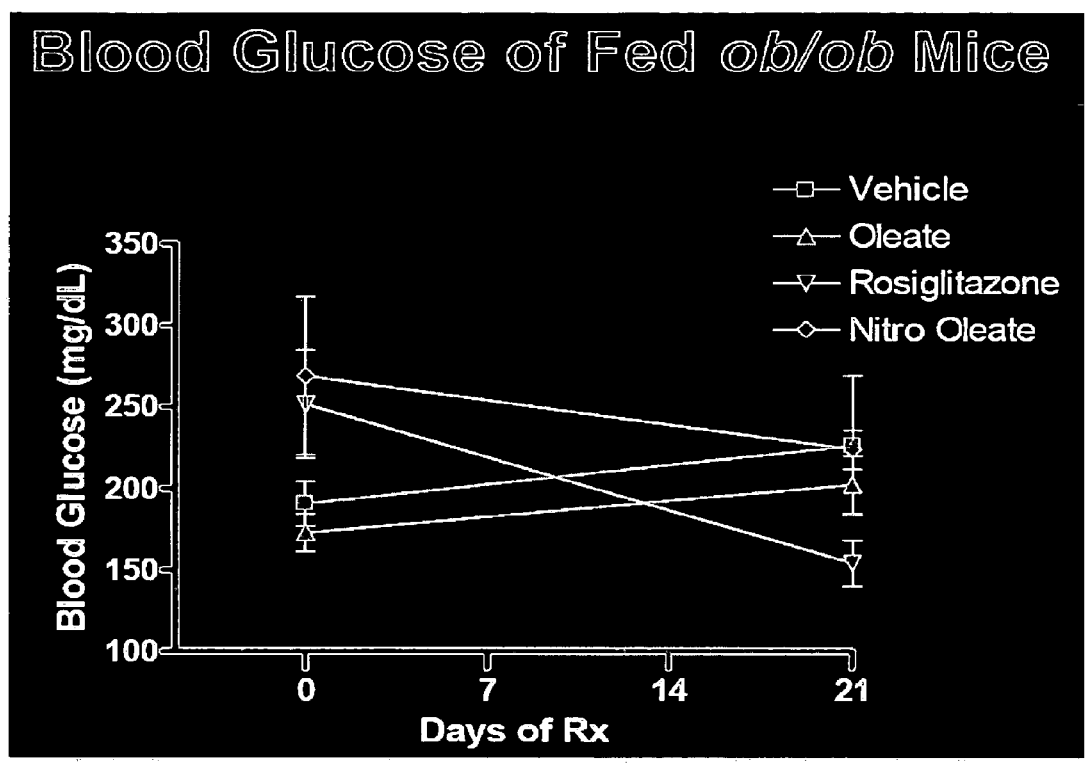
FIG. 3 is a graph that correlates blood glucose levels in leptin-deficient diabetic ob/ob mice on different days after being injected with oleic acid, nitro oleic acid, rosiglitazone, and a vehicle.

In a related vein, the invention encompasses a method for gauging the therapeutic efficacy of the composition as described above. This method involves obtaining at least two blood samples from a subject at different times during treatment and measuring the level of blood glucose in each sample. Indicative of therapeutic efficacy is a lower level of blood glucose in the sample obtained at a later time point during treatment. As shown in FIG. 3, blood glucose levels in ob/ob mice receiving nitro oleic acid are significantly lower on day 21 than at the beginning of the study, indicating the therapeutic benefit of nitro oleic acid in treatment of type 2 diabetes.

What is claimed is:

1. A method for controlling weight gain, comprising the steps of:
   administering to a subject in need thereof a pharmaceutical composition comprising an active agent selected from nitro oleic acid and a metabolite of nitro oleic acid, or a pharmaceutically acceptable salt or prodrug thereof, and a pharmaceutically acceptable excipient, carrier, or combination thereof; and
   repeating the step of administering at least once.

2. The method of claim 1, further comprising, after the administering step, monitoring said subject for a change relating to weight gain.

3. The method of claim 1, further comprising, after at least one repetition of the administering step, monitoring said subject for a change relating to weight gain.

4. The method of claim 1, wherein the active agent is nitro oleic acid.

5. The method of claim 1, wherein the administering step is carried out by oral administration or intravenous drip.

6. The method of claim 1, wherein the pharmaceutical composition is formulated as a solution, suspension, solid, or emulsion.

7. The method of claim 1, wherein the pharmaceutical composition further comprises one or more thickeners, diluents, solvents, buffers, preservatives, surface active agents, excipients, and combinations thereof.

8. The method of claim 1, wherein the pharmaceutical composition further comprises one or more additional therapeutic agents.

9. The method of claim 8, wherein the one or more therapeutic agents are selected from the group consisting of cytokines, and regulators of growth factors.

10. The method of claim 1, wherein the nitro oleic acid comprises a single regioisomer of nitro oleic acid or both regioisomers of nitro oleic acid.

11. The method of claim 1, wherein the pharmaceutically acceptable salt comprises a salt formed by the reaction of nitro oleic acid with an inorganic base selected from the group consisting of sodium hydroxide, ammonium hydroxide, potassium hydroxide, monoalkyl amine, dialkyl amine, trialkyl amine, aryl amine, substituted ethanolamine, and combinations thereof.

12. The method of claim 1, wherein the prodrug comprises a methyl or ethyl ester of nitro oleic acid.

13. The method of claim 1, wherein the pharmaceutical composition further comprises one or more agents to maintain osmolarity selected from the group consisting of sedum chloride, Ringer's dextrose, lactated Ringer's solution, fluid and nutrient replenishers, and combinations thereof.

14. The method of claim 1, wherein the subject is afflicted with type 2 diabetes.

15. The method of claim 1, wherein the subject is a human.

* * * * *